United States Patent [19]

Horodysky et al.

[11] 4,225,488
[45] Sep. 30, 1980

[54] PROCESS FOR MAKING SULFURIZED OLEFINS

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 928,035

[22] Filed: Jul. 25, 1978

[51] Int. Cl.$^3$ ............... C07C 149/10; C07C 149/12; C10M 3/32; C10M 5/22
[52] U.S. Cl. .................................... 260/139; 568/59; 568/18; 252/45
[58] Field of Search ................... 260/139, 608, 609 R; 252/45

[56] References Cited

U.S. PATENT DOCUMENTS

| 2,249,312 | 7/1941 | Kimball | 260/139 |
|---|---|---|---|
| 2,708,199 | 5/1955 | Eby | 260/139 |
| 3,007,911 | 11/1961 | Beretvas et al. | 260/139 |
| 3,068,218 | 12/1962 | Beretvas et al. | 260/139 |
| 3,231,558 | 1/1966 | McMillen | 260/139 |
| 3,471,404 | 10/1969 | Myers | 260/139 |
| 3,697,499 | 10/1972 | Myers | 260/139 |
| 3,703,504 | 11/1972 | Horodysky | 260/139 |
| 3,703,505 | 11/1972 | Horodysky et al. | 260/139 |
| 3,925,414 | 12/1975 | Landis et al. | 260/139 |
| 3,944,539 | 3/1976 | Horodysky et al. | 260/139 |

*Primary Examiner*—Donald G. Daus
*Assistant Examiner*—M. C. Eakin
*Attorney, Agent, or Firm*—Charles A. Huggett; Claude E. Setliff

[57] ABSTRACT

In preparing organic sulfides by reacting olefins (e.g., butylenes) with a sulfur halide to form a sulfohalogenated intermediate which is subsequently sulfurized and dehalogenated by reaction with an aqueous solution of an alkali metal sulfide compound to form a noncorrosive organic sulfide product of high sulfur content, the copper strip corrosion activity is improved by resulfurizing the sulfurized olefin by contacting it with additional aqueous metal sulfide in the presence of a lower molecular weight alcohol, such as isopropanol.

16 Claims, No Drawings

PROCESS FOR MAKING SULFURIZED OLEFINS

BACKGROUND OF THE INVENTION

1. Field of the Invention

The invention relates to the preparation of organic sulfide compounds having improved copper strip corrosion activity.

2. Discussion of the Prior Art

Various proposals have been made for producing organic sulfides by treating olefins with sulfur chlorides and then reacting the resulting intermediate with compounds containing sulfur. For example, organic polysulfides may be prepared by the sulfochlorination of olefins containing 6 or more carbon atoms and further treatment with inorganic high polysulfides according to Eby U.S. Pat. No. 2,708,199. In addition, Meyers U.S. Pat. No. 3,471,404 discloses that sulfurization reactions of this nature may be carried out by reacting a sulfochlorinated isobutylene intermediate produce with a mixture of an alkali metal sulfide and free sulfur in a molar ratio of at least 2:1 followed by a further prolonged treatment with aqueous sodium hydroxide, apparently for reducing high chlorine contents, in producing extreme pressure additives. Beretvas et al. U.S. Pat. No. 3,068,218 indicates that sulfochlorinated products of improved color may be obtained by sulfochlorinating polymers of propylene, etc. containing 8 or more carbon atoms in a aqueous reaction mixture and then sulfurizing the intermediate with a solution of sodium sulfide in water and isopropanol in producing products with sulfur contents of the order of 10 to 34% by weight. In Kimball U.S. Pat. No. 2,249,312, the sulfochlorinated adduct of amylene or higher olefins is treated with sodium sulfide and/or other alkaline compounds to produce stable products of relatively low sulfur content and generally high chlorine contents.

In general, prior art organic sulfide compounds have one or more of such undesirable characteristics as high cost, low sulfur content, high chlorine content and corrosive attack on metals and alloys used in machinery. Products having a chlorine content above 2% and also those produced from sodium polysulfide reactants are usually rather corrosive. Some of these disadvantages can be overcome and organic sulfide compounds having improved properties, especially as to high sulfur content and more desirable corrosion characteristics, are obtained by the economical process described in U.S. Pat. No. 3,703,504. In this process, the aqueous alkali metal monosulfide reactant employed in the final reaction is derived from a spent effluent stream resulting from hydrocarbon purification operations.

SUMMARY OF THE INVENTION

The present invention is concerned with an improved process of preparing organic sulfides by sulfohalogenating an olefin with a sulfur halide (e.g., the bromide or chloride) to form a sulfohalogenated organic intermediate and thereafter sulfurizing and dehalogenating said intermediate by reaction with an alkali metal sulfide, the improvement whereby the corrosion activity of the organic sulfide is enhanced by repeating the reaction with alkali metal sulfide. The invention also includes the product from such process.

DESCRIPTION OF SPECIFIC EMBODIMENTS

The treatment of this invention may be used in conjunction with any processes that involve the sulfohalogenation of olefinic materials. Thus, it can be utilized in any of the aforementioned and other prior art processes in which olefins are sulfohalogenated and subsequently subjected to a sulfurization-dehalogenation reaction in the production of organic sulfides.

A wide variety of olefinic substances may be charged to the initial or sulfochlorination reaction including olefins with terminal or internal double bonds and containing from about 2 to about 12 carbon atoms per molecule in either straight, branched chain or cyclic compounds, and these may be exemplified by ethylene, propylene, 1-butene, cis and trans-2-butene, isobutylene, diisobutylene, triisobutylene, the pentenes, cyclopentene, the hexenes, cyclohexene, the octenes, 1-decene, etc. In general $C_{3-6}$ olefins or mixtures thereof are preferred for preparing sulfurized products for use as extreme pressure additives as the combined sulfur content of the product decreases with increasing carbon content, and the miscibility of the product with oil is lower in the case of propylene and ethylene derivatives.

In some embodiments of the invention, isobutylene is particularly preferred as the predominant olefinic reactant but it may be employed, desirably in major proportion, in mixtures containing one or more other olefins; moreover, the charge may contain substantial proportions of saturated aliphatic hydrocarbons, as exemplified by methane, ethane, propane, butanes, pentanes, etc. Such alkanes are preferably present in minor proportion in most instances to avoid unnecessary dilution of the reaction, since they neither react nor remain in the products but are expelled in the off-gases or by subsequent distillation. However, mixed charges can substantially improve the economics of the present process since such streams are of lower value than a stream of relatively pure isobutylene.

Volatile olefins are often readily available in liquid form, and it is usually desirable to charge olefinic liquids which are vaporized by the heat of reaction, as such evaporation provides a substantial cooling effect that permits the flow of water for cooling the reactor to be reduced considerably for greater economy. Also there are indications that the use of a volatile liquid olefin reactant has the unexpected and desirable effect of lowering the viscosity of the final product.

The other reactant in the first stage is preferably sulfur monochloride ($S_2Cl_2$); but other similar compounds such as sulfur dichloride and $S_3Cl_2$ as well as the corresponding but more expensive sulfur bromides may be employed in an amount which will provide a quantity of sulfur corresponding to desirable reactant ratios for sulfur monochloride. The molar ratio of olefin to sulfur monohalide may range from about 1:1 up to about 1.65:1. In the case of butylenes and sulfur monochloride, the optimum ratio appears to be between about 1.55:1 and 1.60:1.

Although anhydrous reaction conditions are generally regarded as providing better results, a small amount of water ranging up to about 1% of the weight of the sulfur halide may be present in the initial reaction; however, it is usually preferred to keep the water content below about 0.5% on that basis.

The sulfohalogenation reaction is exothermic, evolving 500–650 B.t.u./lb. in the case of isobutylene, and cooling is necessary to prevent the temperature from exceeding about 160° F. with resultant darkening of the product and some decrease in the yield. The preferred range of reaction temperature is from about 120° to 135°

F. and a temperature of about 125° F. appears to be the optimum. Typical reaction times for the initial stage of the process range from about 1 to 15 hours.

The reaction pressure is not critical, and may be illustrated by pressures ranging from about 0 to 100 pounds per square inch gage pressure (p.s.i.g.) depending upon the reaction temperature and the volatility of the olefinic material.

The initial reaction is preferably catalyzed with a lower aliphatic alcohol containing from 1 to 4 carbon atoms, as exemplified by methanol, ethanol, propanol and isopropanol. Of these, methanol and ethanol are usually preferred, especially the former, and amount so the alcohol ranging from about 0.2 to 10% of the weight of the sulfur chloride may be utilized, but quantities of the order of 0.5 to 3% are usually preferred. While the catalytic alcohol may be introduced into the reactor in the liquid state, it is often more desirable to introduce it as a vapor.

Hydrogen chloride is evolved in the reaction and this gas is vented from the reactor. It may be recovered as hydrochloric acid in a water absorption system.

In the second stage of the process of the present invention, an alkali metal sulfide is reacted with the adduct from the first stage. A lower aliphatic alcohol is generally added as a mutual solvent for the sulfurization de-chlorination reaction. Methanol, ethanol, propanol, butanol and isobutanol as well as mixtures thereof may be employed for the purpose, and isopropanol is preferred. Although a quantity of alcohol amount to 10% of the weight of the sulfohalogenation adduct provides adequate solvent action in the reaction mixture, surprising effects are obtained with larger proportions of the alcohol in the reaction mixture in that more alcohol up to a quantity of about 50% of the weight of the adduct not only provides an unexpected increase in the reaction rate but also a striking improvement in sharply reducing the content of undesired chlorine in the final product while increasing its sulfur content. Thus it is desirable to charge at least about 20% alcohol and the range of about 25 to 40% is preferred. While larger proportions of alcohol may provide some additional benefit, the difficulty of handling and recovering the extra alcohol also increases.

In sulfurizing and dechlorinating the sulfochlorination addition product, the aqueous alkali metal monosulfide solution is desirably present in at least a stoichiometric quantity, and preferably a slight excess, of available alkali metal in order to remove most of the combined chlorine from the adduct. Stated another way, the mole ratio of metal sulfide to adduct will range from about 1.0 to about 1.2. In practice, the adduct or intermediate product from the sulfochlorination reaction is pumped into the solution of sodium monosulfide in water and the alcohol in an amount usually ranging from 2.52 to 2.70 pounds of adduct per pound of the sodium sulfide (anhydrous basis) in providing a slight excess of available sodium.

In general, this treatment of the adduct may be carried out at temperatures between about 150° and 250° F. and the range between about 170° and 195° F. is usually preferred. The reaction pressure may be subatmospheric or elevated up to 50 or more p.s.i.g. For simplicity, it is usually preferable to carry out the reaction at reflux temperature of typically 175° to 185° F. under atmospheric pressure in a vessel equipped with a reflux condenser. In a typical production scheme, as disclosed for example in U.S. Pat. No. 3,697,499, the polysulfurized olefin is reacted with alkali metal hydroxide to yield a product having good copper corrosion characteristics. While this treatment yields an excellent product for some applications, it has been found that an 8 hour reaction time with alkali metal hydroxide is difficult to perform and does not always produce a product possessing optimal extreme pressure/antiwear activity.

We have found that by adding to the adduct another portion of metal sulfide, ranging from about 0.2 to 1.2 mole of sulfide to 1.0 mole of adduct, a product having excellent copper corrosion activity is obtained. This can be dissolved in water for addition to the adduct as a 5–25% solution. Or, the aqueous alkali metal monosulfide reactant can be derived from a spent effluent stream resulting from hydrocarbon purification operations such as those described in U.S. Pat. No. 3,703,504, which is incorporated herein by reference. In this step, a lower alkanol, such as isopropanol may be used as described hereinabove. That is, it is used in the quantities specified in the description of the second stage reaction of the adduct with metal sulfide. In general, however, the treatment is milder since the bulk of the reaction has already taken place. The reaction is carried out at from about 150° F. to about 230° F. The range from about 165° F. to about 190° F. is usually preferred. The reaction may be carried out at subatmospheric pressure or up to 50 psig. Preferably it is carried out at atmospheric pressure.

EXAMPLES

Table 1 summarizes the Examples, including proportions of reactants, reaction conditions and the like. In the Examples, the sulfurized olefin, sodium sulfide and 2-propanol were combined and stirred at the temperatures and for the times shown. The sulfurized olefin used was made in accordance with U.S. Pat. No. 3,703,504, Example 1, which employs isobutylene as the olefin.

TABLE 1

| TREATMENT OF SULFURIZED OLEFIN | | | | | |
|---|---|---|---|---|---|
| Example | 1 | 2 | 3 | 4 | 5 |
| Sulfurized Olefin | 300. | 300. | 300. | 300. | 300. |
| Na$_2$S . 9H$_2$O, g. | | 296. | 148. | 74. | 37. |
| Concentration % Na$_2$S in water | | 25% | 25% | 12.5% | 6.3% |
| 2-Propanol, g. | | 150. | 100. | 75. | 50. |
| Sulfurization Time hrs. | | 3 | 3 | 2 ⅔ | |
| Sulfurization Temp., ° F. | | 180 | 180 | 186 | 186 |
| 2-Propanol Distillation, hrs. | | ~½ | ~½ | ~½ | ~½ |
| #of Washes (Distilled water-equal volume) | 3 | 3 | 3 | 3 | 3 |
| Product Drying Final Temperature, ° F. | 190 | ~190 | 200 | 198 | 196 |
| Color | Bright orange | Bright orange | Yellow-orange | Bright orange | Bright orange |
| Final Yield, g. | 283. | 235.5 | 239. | 254. | 255. |

TABLE 1-continued
TREATMENT OF SULFURIZED OLEFIN

| Example | 1 | 2 | 3 | 4 | 5 |
| --- | --- | --- | --- | --- | --- |
| | | | | | |
| | Original | \multicolumn{5}{c}{Examples} | | | | |
| Analyses | Sample | 1 | 2 | 3 | 4 | 5 |
| % Sulfur | 45.1 | 43.7 | 37.5 | 39.6 | 40.2 | 41.6 |
| % Chlorine | 0.38 | 0.33 | 0.12 | 0.14 | 0.13 | 0.17 |
| Specific Gravity | 1.1422 | 1.1308 | 1.0715 | 1.0823 | 1.1058 | 1.1223 |
| Cu Strip Corrosion[(1)] | 2E | 2E | 1A | 1A | 2A | 3A |

[(1)]Determined by placing 3 wt. % of the test compound in a 200" solvent paraffinic neutral mineral oil and testing for 6 hours at 210° F. in accordance with ASTM D-130-9.

We claim:

1. An organic sulfide produced by an improved process comprising the steps of:
    (1) reacting sulfur halide with an olefin, the olefin to sulfur halide molar ratio ranging from about 1:1 to about 1.65:1; and
    (2) reacting the product of (1) with an alkali metal sulfide;
    (3) the improvement comprising reacting the product of (2) with a separate portion of an aqueous solution comprising alkali metal sulfide such that the alkali metal sulfide is present to the extent of from about 0.2 mole to about 1.2 mole of sulfide per mole of the product of (2).

2. The organic sulfide of claim 1 wherein the alkali metal is sodium.

3. The organic sulfide of claim 2 wherein the halide is chloride.

4. The organic sulfide of claim 1 wherein the olefin is isobutylene.

5. The organic sulfide of claim 1 wherein the alkali metal sulfide is sodium monosulfide.

6. An improved process for producing an organic sulfide comprising the steps of:
    (1) reacting sulfur halide with an olefin, the olefin to sulfur halide molar ratio ranging from about 1:1 to about 1.65:1; and
    (2) reacting the product of (1) with an alkali metal sulfide;
    (3) the improvement whereby the product of (2) is reacted with a separate portion of an aqueous solution comprising alkali metal sulfide such that the alkali metal sulfide is present to the extent of from about 0.2 mole to about 1.2 mole of sulfide per mole of the product of (2).

7. The process of claim 6 wherein the alkali metal is sodium.

8. The process of claim 7 wherein the halide is chloride.

9. The process of claim 6 wherein the alkali metal sulfide is sodium monosulfide.

10. The process of claim 6 wherein the olefin has from 2 to 12 carbon atoms.

11. The process of claim 6 wherein the step (1) reaction is run at a temperature not greater than 160° F.

12. The process of claim 6 wherein the temperature is from about 120° F. to about 135° F.

13. The process of claim 6 wherein the step (3) reaction is run at a temperature of from about 150° to about 250° F.

14. The process of claim 6 wherein the olefin is isobutylene.

15. The process of claim 6 wherein the alklai metal sulfide is derived from the spent effluent from hydrocarbon purification operations.

16. The organic sulfide of claim 1 in which the alkali metal sulfide is derived from the spent effluent from hydrocarbon purification operations.

* * * * *

UNITED STATES PATENT AND TRADEMARK OFFICE
CERTIFICATE OF CORRECTION

PATENT NO. : 4,225,488

DATED : September 30, 1980

INVENTOR(S) : ANDREW G. HORODYSKY and PHILLIP S. LANDIS

It is certified that error appears in the above-identified patent and that said Letters Patent are hereby corrected as shown below:

Column 1, line 16, "high" should be --higher--;

Column 1, line 17, "Meyers" should be --Myers--;

Column 1, line 20, "produce" should be --product--.

Signed and Sealed this

Seventeenth Day of March 1981

[SEAL]

Attest:

RENE D. TEGTMEYER

Attesting Officer     Acting Commissioner of Patents and Trademarks